United States Patent
Daniel (10) Patent No.: US 10,342,634 B2
(45) Date of Patent: Jul. 9, 2019

(54) SENSOR-CONTROLLED DISPLAY OUTPUT FOR DIALYSIS MACHINES

(71) Applicant: Fresenius Medical Care Deutschland GmbH, Bad Homburg (DE)

(72) Inventor: Pia Nora Daniel, Bodman (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 244 days.

(21) Appl. No.: 15/360,324

(22) Filed: Nov. 23, 2016

(65) Prior Publication Data
US 2017/0172695 A1    Jun. 22, 2017

(30) Foreign Application Priority Data
Dec. 21, 2015   (DE) .......................... 10 2015 122 347

(51) Int. Cl.
*G06F 3/0484*   (2013.01)
*A61M 1/14*     (2006.01)
(Continued)

(52) U.S. Cl.
CPC ............... *A61B 90/37* (2016.02); *A61M 1/14* (2013.01); *A61M 1/16* (2013.01); *A61M 1/1652* (2014.02);
(Continued)

(58) Field of Classification Search
CPC .. G06F 3/04842; G06F 3/04847; G06F 9/453; G06F 3/0482; G06F 3/14;
(Continued)

(56) References Cited

U.S. PATENT DOCUMENTS

| 2007/0061089 A1* | 3/2007 | Liu ..................... A61M 1/3639 702/50 |
| 2014/0263063 A1* | 9/2014 | Jones ..................... A61M 1/16 210/647 |
| 2015/0227293 A1* | 8/2015 | Stenquist ............ A61M 1/3607 715/765 |

FOREIGN PATENT DOCUMENTS

| DE | 692 26 181 T2 | 1/1999 |
| EP | 0 623 357 A1 | 11/1994 |
(Continued)

OTHER PUBLICATIONS

International Patent Application No. PCT/EP2016/081000, Search Report (dated Mar. 24, 2017).
(Continued)

*Primary Examiner* — Aaron Lowenberger
(74) *Attorney, Agent, or Firm* — Leydig, Voit & Mayer, Ltd.

(57) ABSTRACT

A medical apparatus, such as a dialysis machine (e.g. a hemodialysis machine or a peritoneal dialysis machine), includes a plurality of components, one or more sensors corresponding to the components and configured to detect signals, a display and a control unit. The control unit is configured to: receive signals from the one or more sensors, determine, from the signals, a status of the medical apparatus, and determine control commands for the display based on the determined status for status-dependent control of the display. The described apparatus improves the human-machine interface in terms of set-up time, operating time and freedom from errors. Depending upon the determined status, different status-specific menus may be illustrated on the display in order to assist the user when operating the apparatus or advise the user about any errors or subsequent steps.

17 Claims, 4 Drawing Sheets

(51) Int. Cl.
  *A61B 90/00* (2016.01)
  *G06F 9/451* (2018.01)
  *A61M 1/36* (2006.01)
  *G06F 3/0482* (2013.01)
  *G06F 3/14* (2006.01)
  *A61M 1/16* (2006.01)
  *G16H 40/63* (2018.01)

(52) U.S. Cl.
  CPC ......... *A61M 1/3672* (2013.01); *G06F 3/0482* (2013.01); *G06F 3/04842* (2013.01); *G06F 3/04847* (2013.01); *G06F 3/14* (2013.01); *G06F 9/453* (2018.02); *G16H 40/63* (2018.01); *A61M 2205/3327* (2013.01); *A61M 2205/3592* (2013.01); *A61M 2205/502* (2013.01); *A61M 2205/505* (2013.01); *A61M 2205/583* (2013.01)

(58) Field of Classification Search
  CPC ......... A61B 90/37; G16H 40/63; A61M 1/14; A61M 1/3672; A61M 1/16; A61M 1/1652; A61M 2205/3327; A61M 2205/502; A61M 2205/583; A61M 2205/3592; A61M 2205/505
  See application file for complete search history.

(56) References Cited

FOREIGN PATENT DOCUMENTS

| | | |
|---|---|---|
| WO | WO 2004/103442 A1 | 12/2004 |
| WO | WO 2013/074769 A2 | 5/2013 |
| WO | WO 2013/116660 A1 | 8/2013 |
| WO | WO 2014/162000 A1 | 10/2014 |

OTHER PUBLICATIONS

German Patent Application No. 10 2015 122 347.3, Office Action dated Aug. 9, 2016.

\* cited by examiner

SENSOR-CONTROLLED DISPLAY OUTPUT FOR DIALYSIS MACHINES

CROSS-REFERENCE TO RELATED APPLICATIONS

Priority is claimed to German Patent Application No. DE 102015122347.3, filed on Dec. 21, 2015, the entire disclosure of which is hereby incorporated by reference herein.

FIELD

The present invention relates to a control unit, a dialysis machine or another medical apparatus and a method and a computer program for the sensor-controlled display actuation for a dialysis machine,

BACKGROUND

Known, modern medical-technical apparatuses, in particular dialysis apparatuses, e,g. the hemodialysis apparatus 5008 from Fresenius Medical Care, require, for the setting up of the machine or for operating the machine, a sequence of operating steps and actions which have to be performed on the machine or on connected components, such as e.g. a heparin pump. For the operating steps to be performed, the user is assisted and guided by a suitable illustration on a display of the machine. The display can be, for example, a touch-sensitive screen, a touch-screen, for controlling the apparatus and for inputting and outputting data. Capacitive sensor technology is usually used for the touch-sensitive operating interfaces of the dialysis apparatuses. A touch-screen having capacitive sensor technology is described in more detail for example in U.S. Pat. No. 9,189,597, the entire disclosure of which is hereby incorporated by reference herein, The hemodialysis system includes, as a central unit, a dialysis apparatus which is used to continually guide blood from a patient into an extracorporeal technical circulation module through a blood chamber of a filter or of a dialyzer. The blood chamber is separated from a dialysis fluid chamber by a semi-permeable membrane. The dialysis fluid chamber has a dialysis fluid, which contains blood electrolytes, flowing therethrough. The material concentration of the dialysis fluid corresponds to the concentration of the blood of a healthy person. During treatment, the blood from the patient and the dialysis fluid are guided past both sides of the membrane generally in opposite flow directions at a predetermined flow rate. The urinary excretion products diffuse through the membrane from the blood chamber into the chamber for dialysis fluid, whilst at the same time electrolytes provided in the blood and in the dialysis fluid diffuse from the chamber of higher concentration to the chamber of lower concentration. The metabolism can be additionally influenced by applying a transmembrane pressure.

In order to carry out the above-described functionality, the medical apparatus having the extracorporeal blood circulation module comprises a plurality of technical components, such as substitute fluid pumps, valves, restrictors, pressure sensors and technical elements and devices, such as external connections, sliding handles, blower filters, an electrical connection, hydraulic connections having flaps, etc. In order to set up and operate the dialysis system, the above-mentioned technical components and devices are operated frequently in a tailored sequence of several operating steps. The execution of operating steps on the different technical components of the machine can lead to errors or error conditions which adversely affect the operation of the dialysis apparatus or even render the operation impossible. Ensuring correct operation is therefore important. Errors should fundamentally be avoided and recognized as soon as possible. To this end, it is known from the prior art to output particular indications on a display of the dialysis machine, the user being assisted by said indications when performing the operating steps. A predetermined fixed menu is provided and output. The user thus receives indications regarding a sequence of operating steps to be carried out in sequence.

SUMMARY

In an exemplary embodiment, the invention provides a medical apparatus. The medical apparatus includes: a plurality of components; one or more sensors corresponding to one or more of the plurality of components, configured to detect signals, a display; and a control unit, configured to: receive signals from the one or more sensors, determine, from the signals, a status of the medical apparatus, and determine control commands for the display based on the determined status for status-dependent control of the display.

In another exemplary embodiment, the invention provides a method for controlling a display of a medical apparatus. The method includes: detecting, via one or more sensors of the medical apparatus, sensor data which represent a status of the medical apparatus; and determining, by a control unit of the medical apparatus, control commands for controlling the display based on the status of the medical apparatus.

In yet another exemplary embodiment, the invention provides a non-transitory computer-readable medium having processor-executable instructions stored thereon for controlling a display of a medical apparatus. The processor-executable instructions, when executed, facilitate performance of the following: detecting, via one or more sensors of the medical apparatus, sensor data which represent a status of the medical apparatus; and determining, by a control unit of the medical apparatus, control commands for controlling the display based on the status of the medical apparatus.

BRIEF DESCRIPTION OF THE FIGURES

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Known systems have proved to be disadvantageous in that the illustration on the display by a predetermined menu with a fixed menu structure is defined in an invariable manner. The menu runs in a fixed sequence so to speak. However, it has been shown in practice that more flexibility is desired in this regard. In particular, a display illustration should be possible which is adapted to the current specific situation. e.g. if the user has performed certain operating steps in error, it is desirable if display illustrations including corrective indications are output, even if the user is already in a different menu. Therefore, correct implementation of a respective operating step should be checked and a result-based display illustration should be triggered depending upon the result of the check, and therefore, for example in the event that an error is detected, a modified menu structure can be provided and, for example, an indication can be output stating that an error has been detected in a particular component, if need be outputting further corrective measures.

Since the operation of the apparatus occasionally concerns life-sustaining measures for the patient, ensuing correct operation of the apparatus with all preparation steps is of utmost importance for the safety of the system. In this context, the invention aims to improve the human-machine interface.

Exemplary embodiments of the present invention improve the operation of dialysis apparatuses and other medical apparatuses and in particular make them safer. Furthermore, during apparatus operation using a plurality of different components, the status of all of the components is to be monitored, in particular for freedom from error. The result of the monitoring should influence an improved display actuation, through which it is possible to trigger the illustration on the display in dependence upon a status of the apparatus and the components thereof.

Exemplary embodiments of the invention include a control unit, a medical apparatus and a method and a computer program product.

In an exemplary embodiment, the invention is described with reference to a device and a control unit. In so doing, features, advantages or alternative embodiments mentioned are also applicable to other exemplary embodiments. For example, features discussed with respect to an apparatus or a control unit may also be applicable with respect to a method. Additionally, for example, functional features of the method may be embodied by corresponding modules, in particular by electronic circuitry components or microprocessor modules, of an exemplary system or device and vice versa.

In an exemplary embodiment, the invention relates to a control unit for actuating a display for operating a medical apparatus, in particular a dialysis apparatus. A sensor unit is provided on the medical apparatus which is configured to detect physical signals and relay the same to the control unit. The control unit is configured to automatically determine, from the detected signals, a status of the medical apparatus and to calculate, via control logic, control commands for actuating the display depending upon the status, and preferably also to output said control commands.

Basically, the control unit relates to an electronic module for a sensor-based and status-dependent outputting of graphical signals and optionally corresponding control commands for actuating the display or for outputting on the display. Depending upon the detected status, different status-specific menus should be illustrated on the display in order to assist the user when operating the apparatus and/or advise said user about any errors and/or subsequent steps.

A preferred embodiment of the invention relates to components for receiving or inserting disposable articles, such as for example heparin syringes, in a heparin pump of a dialysis machine, and the operation of the components and the check thereof for freedom from errors via a correspondingly specifically designed user guide on the display. Other embodiments of the invention relate to other components, such as for example other pumps, holding devices—e.g. for a dialysis filter—and/or connections on the dialysis apparatus and/or receiving devices for medical components or disposable articles.

The control unit is an electronic unit which can be embodied in hardware as an integrated circuit (e.g. as a field-programmable gate array (FPGA)) or in software. The control unit is used for display actuation. The control unit can be implemented directly in a graphics card or in a graphics chip or indirectly on a processing unit which exchanges data with the graphics card and with the display. The graphics card writes data for the display to a graphics memory which is typically formed as a random access memory (RAM). The processor unit and/or the graphics chip or the graphics card read the memory in order to display the stored data on the display. Optionally, a video adapter can be implemented which uses the digital signals of the control unit and/or an application program, stores same in the memory (e.g. Video RAM) and outputs same or, if necessary, converts the digital signals into an analogue signal (using a D/A converter). The control unit in accordance with the invention exchanges data with the sensor unit. This can preferably be via a unidirectional data connection, via which the sensor unit sends detected sensor data to the control unit. The sensor data represent a status of the medical apparatus having preferably all of the components connected to the apparatus. In a simpler embodiment of the invention, only a selection of the components can be fitted with corresponding sensors, the status of which is then considered. The sensor data are converted, via control logic of the control unit, into control commands for status-dependent actuation of the display for outputting signals on the display.

The control logic is an integrated circuit and/or a program which determines how the sensor data which can originate from the different sensors are calculated and which display output is to be produced in each case on the basis of the detected data.

The sensor unit comprises a plurality of sensor modules. For their part, the sensor modules comprise a plurality of sensors. The sensor modules are installed on the dialysis apparatus, preferably at a plurality of positions in the apparatus, and on all or selected components of the apparatus and/or on the respective interfaces between the apparatus and components. The sensors are preferably installed as sensors of different sensor types and also include, in addition to optical sensors, acoustic sensors, position and/or proximity sensors, temperature sensors, Hall effect sensors and other sensor types, switches, buttons and/or potentiometers, etc.

The medical apparatus utilizes, for operation, a multiplicity of technical components, such as pumps, tubes or other mechanical and/or electronic units which are to be connected to the apparatus or are already integrated therein. As already mentioned above, in a preferred embodiment of the invention, the component is a heparin pump. Other embodiments of the invention refer to other pumps, dialysis filters in dialyzers, clamps, modules or devices as components. The components can also be configured to receive disposable articles, such as tubes, filters, disposable syringes, etc. In a preferred embodiment of the invention, each component is formed with at least one sensor. The component is operated. For example, a heparin syringe should be correctly inserted and connected into the pump, provided for this purpose, on the apparatus before said apparatus can be put into operation. It is thus appropriate to perform a sequence of particular operating steps on the apparatus and/or on the component. In accordance with the invention, this sequence is monitored by the sensor unit.

The set of all the sensor signals represents a status of the apparatus or of the machine with its components. The status includes a plurality of status variables which are dependent upon the respective application and the components being used. For instance, the status can be defined inter alia, for example, by the status variable "doors or cover on the dialysis apparatus 5008 closed or open?". This is detected by one or more suitable sensors (e.g. positional sensors). For example, the dialysis machine can only be set up with the blood tube system when the cover is open. Prior to opening the cover, an illustration of menu points which relate to subsequent actions for connecting or operating the blood tube system is meaningless or even confusing for the user because said user cannot (yet) perform these actions in the current status. In accordance with the invention, these menu points are also not displayed in the yet unopened status, but rather a display is output indicating to the user e.g. that doors need to be opened. Generally, in order to set up or operate the machine, a plurality of actions, interventions (using connected technical devices or manually actuated), process steps or operating steps are to be carried out on different components. It may be required to follow a particular sequence when operating the individual component and/or when performing the individual operating steps. In accordance with the invention, dependent upon the calculated status which is based on the detected sensor data, a specifically generated menu structure is produced for this purpose with a corresponding sequence of display outputs which assist the user in the specific application depending upon the status.

In a preferred embodiment of the invention, the control unit includes a switch or button for determining a menu type. Two different menu types are fundamentally provided: a step-by-step mode which produces a display illustration for each operating step of a sequence of operating steps and displays same in sequence in a suitable manner for the implementation of the operating steps on the apparatus. An operating step on the apparatus or on one of the components can be allocated to a graphical output with a corresponding display illustration. The respective graphical output can in turn comprise a plurality of subordinate graphical outputs (e.g. in the form of menu sub-pages). As a result, the user is guided through the sequence of operating steps by the illustration of the sequence of menu pages. Furthermore, a parameter-based mode is provided in which machine parameters can be adjusted directly. This has the advantage that an experienced user does not have to click through the entire menu but rather can input the respective settings directly. The switch or button can also be formed as a so-called touch-key on the display. Furthermore, instead of the switch or button, a determining unit which is operated automatically or semi-automatically can be provided and is configured to detect or determine the menu type.

The display is a user interface (also called a monitor). It is preferably formed as a touch-sensitive display and comprises a sensor (touch-screen sensor) for detection of the input signals (e.g. on input fields) for control and operation of the dialysis apparatus (hereinunder also called the apparatus or machine) with its components and a display on which interaction surfaces, switching elements, control fields etc. for control of the dialysis apparatus are illustrated. The display is used in particular for illustrating a specifically produced menu having a sequence of different menu pages for—controlling or operating the medical-technical apparatus. The menu is displayed prior to or during the implementation of operating steps on the apparatus and is used to guide the user when carrying out the operating steps or to provide said user with additional information. The display is therefore an input/output unit or user interface for inputting and outputting signals. The display is preferably formed as a capacitive touch-screen. Preferably, the touch-screen has a multi-sensor functionality so that simultaneous touches can also be detected. An example of such a touch-screen is described, as mentioned above, in more detail in U.S. Pat. No, 9,189,597. Typically, the touch-screen comprises, in addition to the display (the actual display unit), a touch-screen sensor as an input unit for user signals, a controller and optionally a driver which can be arranged in the medical apparatus. In an alternative and likewise preferred embodiment of the invention, the touch-screen sensor can be designed as a projected capacitive sensor (usually termed a "PCT"—"projected capacitive touch" or "PCAP"). The sensor thus uses two planes with a conductive pattern (e.g. stripes or lozenges). The planes are provided in a manner insulated from one another. If a finger is located on the crossing-point of two stripes, the capacitance of the capacitor changes and a greater signal arrives at the receiver stripe. This signal change can therefore be precisely measured with the aid of the X and Y coordinates, wherein a plurality of touch points can also be defined exactly. The current flow from the corners of the touch-screen to the touch point is proportional to the XY coordinates. The substantial advantage of this system is that the sensor can be attached to the rear side of the cover glass since the touch recognition is "projected through" the glass. Operation thus takes place on the virtually actually wear-free glass surface. Furthermore, it is possible to recognize gestures and multiple touches (i.e. multi-touch). In other embodiments of the invention, however, resistive or inductive or other sensor technologies can also be used for touch-screens.

The invention is described hereinunder for a dialysis apparatus as an example of a medical apparatus, e.g. of a hemodialysis apparatus or of a peritoneal dialysis apparatus. However, for the person skilled in the art it will be appreciated that the invention can likewise be applied or transferred to other medical-technical computerized apparatuses or (fluid-management) machines or blood-treatment apparatuses which have a display for displaying apparatus data and/or are controlled via the display.

In a preferred embodiment of the invention, the status is occasionally defined by the current or by the planned operation of the apparatus. The current status is detected by the sensor unit and thus relates to an ACTUAL status of the system with all its components. In one embodiment, a predicted probable consequence status can be calculated from the detected ACTUAL status. For instance, e.g. suitable sensors can detect whether a single-needle or a double-needle operation or operation having a substitute fluid pump is to he performed. After detecting the status, status-dependent output signals are then automatically produced in accordance with the invention tier displaying on the display. After, for example, the sensor unit has automatically detected that the single-needle pump is to be fitted, the control unit in accordance with the invention automatically recognizes that a single-needle operation is to be performed (consequence status) and produces output signals and corresponding actuation commands in order to display a menu for setting up the machine for single-needle operation.

In a preferred embodiment of the invention, the sensor unit is arranged on ail the components. In simpler embodiments, sensors from the sensor unit are formed only on relevant and selected components. The sensor unit comprises at least one and preferably a plurality of sensors on different components and/or at different positions and/or components of the medical apparatus. The sensors are formed to detect different technical signals, in particular physical, electrical and/or chemical measurement variables. The sensors can be formed as an optical sensor (e.g. in the form of a camera), as an acoustic sensor, Hall effect sensor, position sensor and/or sensor for detecting other signals. The sensor unit can comprise at least one of the sensors mentioned above, a switch, button and/or a potentiometer, In a preferred embodiment of the invention, the control unit comprises a sensor trigger switch, via which it can be activated and deactivated. Operation of the sensor unit can thus be turned on or off in an advantageous manner.

In an exemplary embodiment, the invention provides a medical apparatus, in particular a dialysis apparatus, which is operated and controlled via a display having the following modules which exchange data:
  a control unit, as described above;
  a plurality of technical components which are connected to the medical apparatus or are configured for connection thereto (and are still to be connected) and must be operated for setting up or operating the medical apparatus;
  a display on which display outputs are output from a graphics memory for operating the medical apparatus and/or the components thereof. The display outputs can be menu illustrations, produced depending upon the status, having sub-menu pages;
  a sensor unit which is arranged on the medical apparatus and in particular on the components thereof and which is configured to automatically detect a status of the medical apparatus with all or selected components and to relay same to the control unit for calculating the control commands.

in an exemplary embodiment, the invention provides a method for actuating a display of a medical apparatus, in particular a dialysis apparatus, which is operated and controlled via the display, comprising the following method steps:
  detecting sensor data which represent a status of the medical apparatus with its components,
  calculating control commands for actuating the display in dependence upon the status and the detected sensor data.

in a preferred embodiment of the method, the control commands are also further applied to output a display illustration in dependence upon the detected sensor data. This has the advantage that the user is assisted when operating the apparatus via the graphics output which is specifically produced in dependence upon the status.

In a further preferred embodiment of the method, the status includes at least one status variable. Preferably, each status variable characterises a status of each component. In particular, the status thus includes all the status variables or statuses of all the relevant components. The status variable can have only one parameter and can thus be formed as a binary signal ("1" or "0") (e.g. representative of "door open" or "door closed"). Alternatively, the status variable can also include a plurality of parameters (e.g. as a distance signal).

Operation of a respective component generally utilizes a sequence of operating steps which are to be performed on the apparatus or on the component. In the step-by-step mode, each operating step is allocated to at least one display output. This has the advantage that the user receives an instruction or indication for each operating step. Preferably, the produced graphics are output with the respective menu in terms of time before the operating step is performed and thus as an indication and instruction. Likewise, it is possible to implement the produced signal output with the menu to be illustrated only after the operating step is performed and thus as a confirmation for a correct operating step or an erroneous or omitted operating step as a corrective and checking output.

The output on the display can be an interactive user guide with a sequence of preferably hierarchically structured operating menu illustrations with sub-menu illustrations for each component. The sequence of operating menu illustrations is determined in dependence upon the detected sensor data (and thus dependent upon the status). In accordance with the invention, an amended display output is produced and output even during the illustration of a menu on the display, if a particular status is detected via the sensor unit, said status requiring an indication to be output. This amended display output is also displayed if the status refers to another component. If for example, the menu for connecting the substitute fluid pump is displayed but at the same time it is detected that an error is occurring when inserting the heparin syringe in the heparin pump, then the previous menu is interrupted so to speak and an image page is output which includes corrective indications to obviate the error when inserting the heparin syringe. In an alternative embodiment of the invention, a configuration can be established that a graphics output is output for precisely the component on which a status change has been detected. This has the advantage that only current and relevant graphics outputs are output and in particular those which relate to component which have just been operated at that time. Furthermore, a configuration can be established as to when and how the status-dependent graphics outputs are output. For instance, an adjustment can be made that the amended graphics output produced in accordance with the invention is overlaid as an additional window over the previous display (as a pop-up or float-in window) and/or that the output is to be output directly and without a time delay or subsequently with a time delay, e.g. only after running through a menu currently output on the display (so as advantageously not to confuse the user with different instructions).

In a further preferred embodiment, the outputting is effected on the display for interactively guiding the user during the operation or during the setting up of the medical apparatus. In dependence upon the detected sensor data, an operating menu illustration is produced for the respective component (on which the sensor data have been detected) or is already pre-configured and is selected for display.

In an exemplary embodiment, the invention provides a computer program product for a medical apparatus which is, or can be, loaded in a memory of a computer or of an electronic or medical-technical apparatus, with a computer program to carry out the method described in more detail above, when the computer program is executed on the computer or the electronic or medical-technical apparatus.

The computer program product can be loaded in an internal memory of a digital control unit.

In an exemplary embodiment, the invention provides a computer program for carrying out all method steps of the method described in more detail above when the computer program is executed on a computer or an electronic or medical-technical apparatus. It is thus also possible for the computer program to be stored on a medium which can be read by the computer or the electronic or medical-technical apparatus.

In the following, a detailed description of the figures, exemplified embodiments, which are not to be understood to be limiting, together with the features and further advantages thereof, are discussed with reference to the drawings.

The invention will be explained in more detail with reference to exemplified embodiments with reference to the figures.

The invention improves the human-machine interface in terms of the set-up time, operating time and freedom from errors. User errors can be avoided by the status-specific production of a display output on the display D with a detailed display of operating steps. This relates initially to all the operating interventions on the medical apparatus 20 and the components 200 thereof, and in particular to those components which are configured for inserting disposable articles, such as for example pumps or couplings for tubes, etc.

The invention relates in particular to an automatic detection of interventions on the medical apparatus 20 and the components 200 thereof via a sensor unit S for the status-dependent display output in terms of a user guide when controlling the apparatus.

Figure 1:
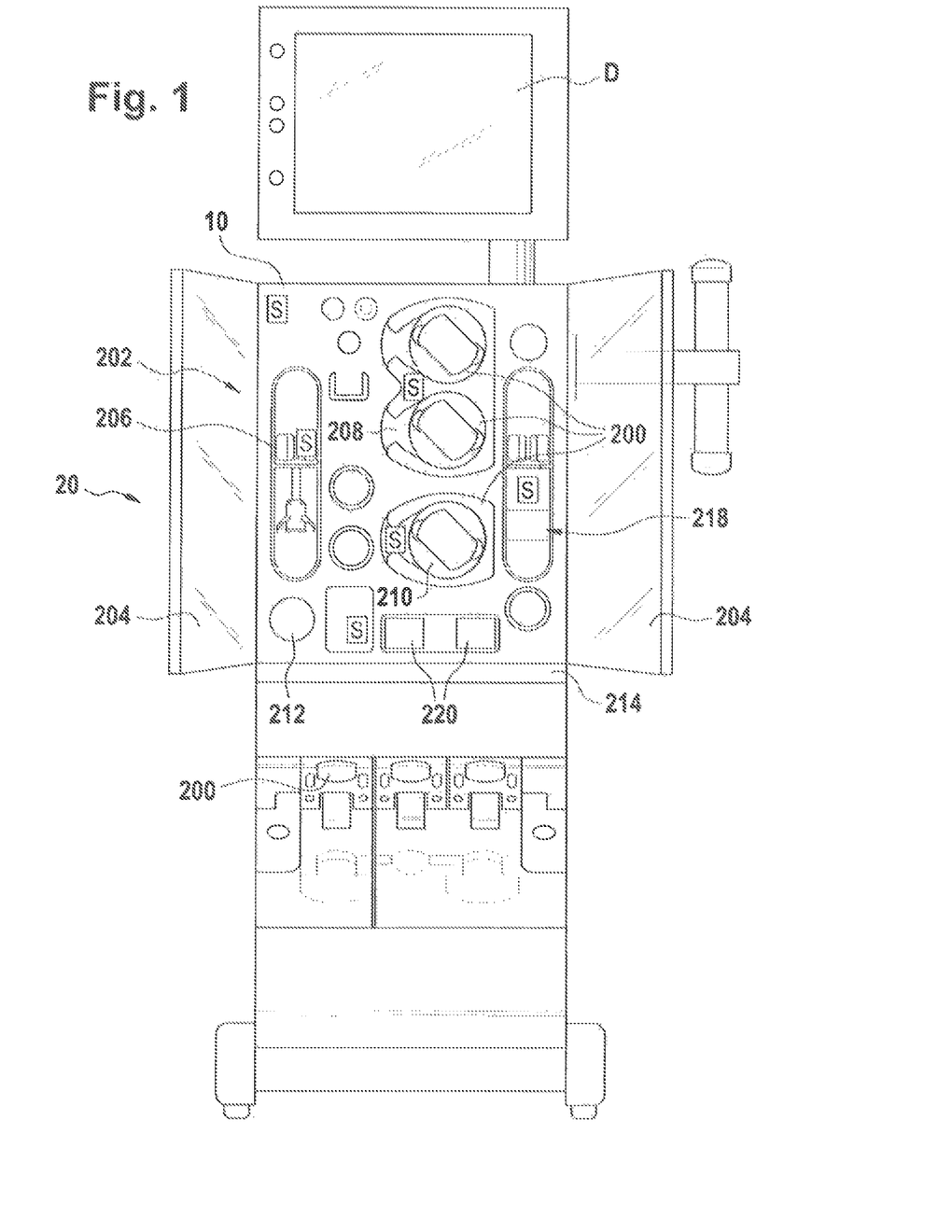
FIG. 1 shows a basic view of a dialysis apparatus having a display in accordance with a preferred embodiment of the invention.

FIG. 1 shows a basic view of a dialysis apparatus representing a medical apparatus 20. The dialysis apparatus is operated and controlled via a connected display a in accordance with the invention, a control unit 10 is connected to the medical apparatus 20 via a suitable data connection. As schematically shown in FIG. 1, the dialysis apparatus includes an extracorporeal treatment module 202 as a central element. This is prevented from being inadvertently contacted by a transparent cover 204 which, in this case, is in the form of a two-leaf door. The extracorporeal treatment module 202 includes a multiplicity of components 200 in the form of different pumps (e.g. blood, substitute fluid), valves, syringes, holders, receptacles and the like. The medical apparatus 20 also includes other components 200. The components 200 can be located at different positions either within the medical apparatus 20 or externally (on a connected component), i.e. also outside of the extracorporeal treatment module 202. Furthermore, the components 200 themselves can also be connected as an external, separate device to the dialysis apparatus via a corresponding connection and a data connection. In the exemplary embodiment illustrated in FIG. 1, a blood pump 208 is shown in the upper central region of the extracorporeal treatment module 202. Located beneath it is a substitute fluid pump 210 and, on the left-hand side below a heparin pump 206, a substitute fluid port 212. Located on the lower part of the extracorporeal treatment module 202 is a channel 214 having a leakage sensor for the extracorporeal treatment module 202. As well as different measuring heads 220. On the right-hand side, a component group 218 is formed for venous filling level and air monitoring, which group can include, for example, an optical detector and an air bubble detector, a tension lever having a filling level detector (shown in the center) having a tube receptacle or tube guide (in the upper region) and a bracket for a venous bubble trap. Furthermore, other measuring units, connections and/or other components can be formed in the extracorporeal treatment module 202.

In accordance with the invention, a sensor unit S is provided which includes a multiplicity of individual signal pick-ups or sensors. The separate sensors can be of a different type or can detect the same physical variables. For example, optical sensors, position sensors, end position sensors, Hall effect sensors or sensors of a different type can be provided. The sensors are either integrated or attached directly on the dialysis apparatus or indirectly on the components 200 of the dialysis apparatus. The components 200 are used to operate or control the medical apparatus 20. The components 200 can also be designed to be connected to other components (e.g. connections, tubes etc.). Furthermore, the components can also be used to receive disposable articles (e.g. syringes, tubes).

In a preferred embodiment, the invention relates to a heparin pump 206 as a component, which is configured to be used with a heparin syringe (not shown in FIG. 1).

As briefly mentioned above, the components 200 can also be located within the medical apparatus 20 and in particular within the extracorporeal blood treatment module. They can be, e.g., filters or pumps. These components 200 should be maintained and/or repaired in the event of a malfunction. To this end, the extracorporeal blood treatment module should be opened (e.g. by opening a front side outwards). The status of being opened can likewise be detected by the sensor unit S in accordance with the invention and be relayed to the control unit 10. The control unit 10 can be configured to synchronize these sensor data with maintenance planning data which are preferably read from a central server or a monitoring unit via a further provided (preferably network-based) interface. If the synchronization shows that the apparatus 20 is open (sensor signal) and that maintenance work is planned in this time frame (server data), then a conclusion can be made in accordance with the invention that maintenance is to be expected as the next operating intervention. Accordingly, a respectively allocated menu (in this case: for maintaining the respective component, e.g. As menu start image page 500) is output on the display D.

Figure 3A:
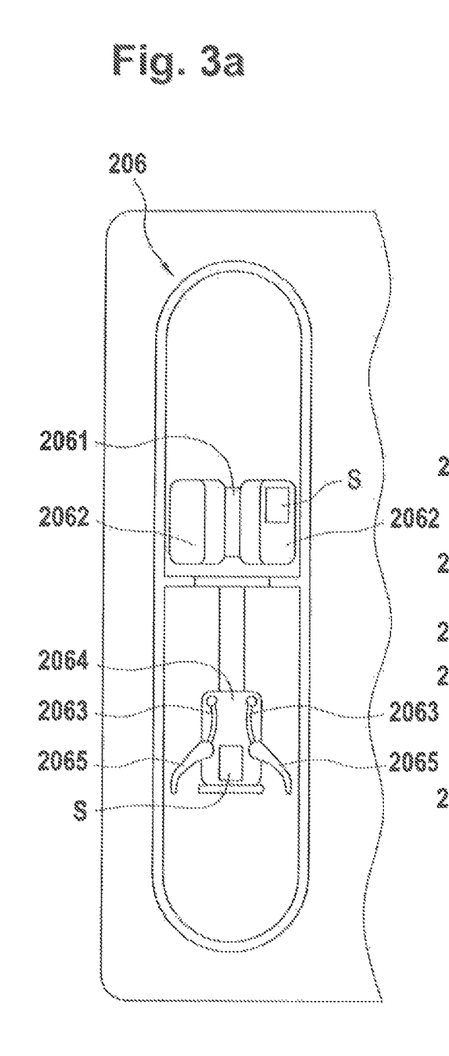
FIG. 3a shows a heparin pump without an inserted heparin syringe.
Figure 3B:
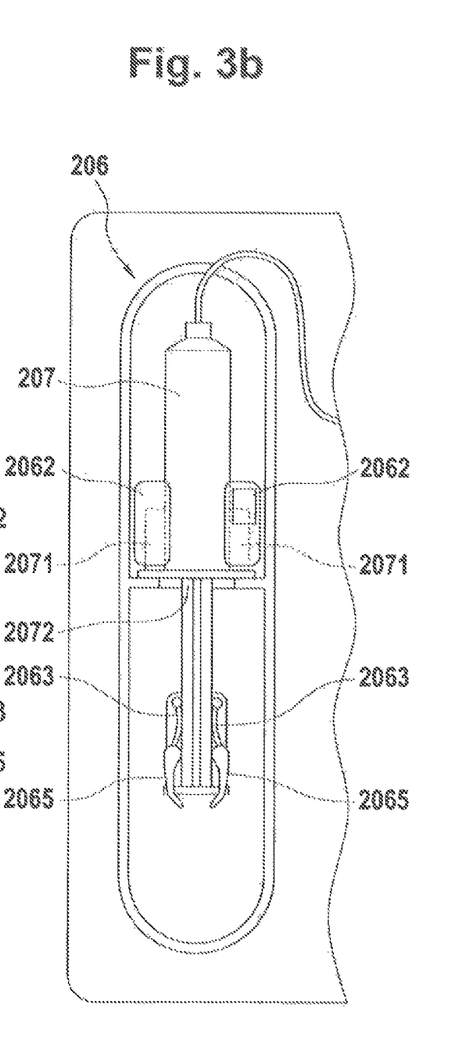
FIG. 3b shows a heparin pump with an inserted heparin syringe.

The heparin pump 206 illustrated in FIG. 1 is shown and described once again in further detail in FIGS. 3a and 3h. FIG. 3a shows the heparin pump without an inserted heparin syringe and FIG. 3b shows the pump with an inserted heparin syringe 207. For the operation of the dialysis apparatus, the heparin syringe 207 for the respective application should be correctly inserted in the heparin pump 206 and locked therein. To this end, the heparin pump 206 comprises a tension lever 2061 having syringe recognition, holding brackets 2062, clamps 2063, a handle 2064 and a clamping lever 2065.

The components mentioned above should be operated correctly. In accordance with the invention, depending upon the detected status, the following warnings can be output on the display D for example:

"In order to automatically check whether the heparin syringe is correctly fixed and connected, this should be inserted before the purge volume is reached."

"Only heparin syringes having a volume of less than or equal to 30 ml can be used."

The display D, also called a monitor, is used as a human-machine interface for inputting and outputting signals and indications for operating the medical apparatus 20 with its components 200.

Figure 2:
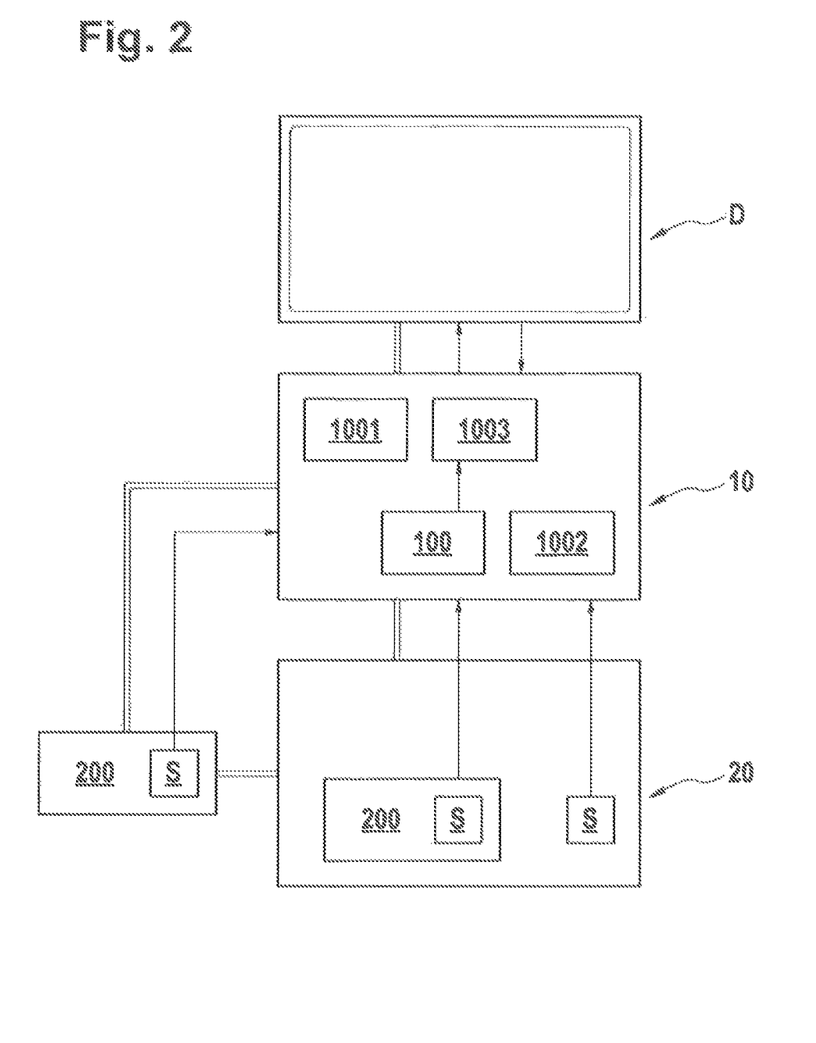
FIG. 2 shows a schematic view of a dialysis apparatus having a control unit in accordance with the invention and a medical apparatus.

FIG. 2 schematically depicts further components of the medical apparatus 20 and of the control unit 10. A driver 1001 can be arranged in the control unit 10 or in the medical apparatus 20, while a controller 1002, which can be designed as a micro-controller, is arranged directly in the display D or even in the control unit 10 or constitutes the connection thereto and is designed, so to speak, as an interface. Alternatively, the controller 1002 can also be designed as a separate entity which is attached via a data connection. The control unit 10 includes a logic circuit or control logic 100. The control logic 100 is used to calculate, from the signals received by the sensor unit S, a status of the medical apparatus 20 with all its components 200 and, in dependence upon the calculated status, to produce control commands in order to produce a case-specific display output and to store same in a graphics memory 1003 and then to read this for illustration on the display D. As shown in FIG. 2, normally different entities of the sensor unit are formed, i.e. different sensors which are arranged or integrated on different components and at different positions on the apparatus 20 and the signals therefrom are transmitted to the control unit 10 for automatic calculation. The sensors can be integrated directly on the medical apparatus 20 and/or indirectly on components 200 of the apparatus 20. The components 200 can thus also be located outside the apparatus 20 and exchange data therewith and/or be connected thereto in another manner.

Figure 4:
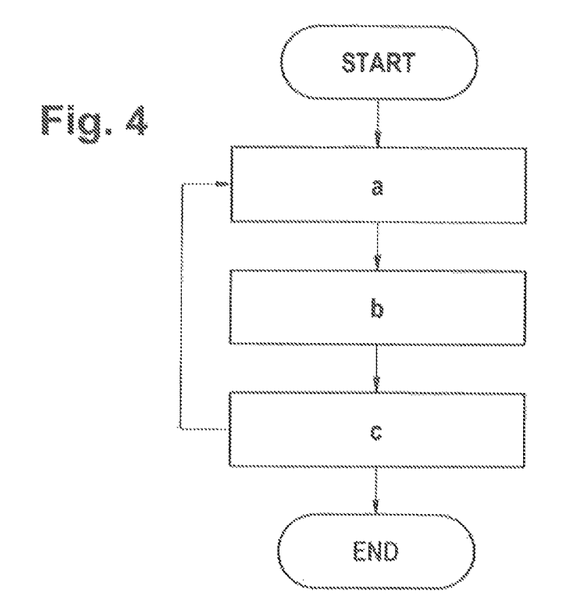
FIG. 4 shows a flow diagram in accordance with a preferred embodiment.

FIG. 4 shows a flow diagram in accordance with a preferred embodiment of the invention. After the system is started, sensor data are detected in step a. Depending upon the configuration of the method, all the sensors of the sensor unit S can be polled or only a predefined selection of sensors can be polled. The latter option has the advantage that the amount of data to be transmitted and calculated does not become too large and the duration of the method can be kept as short as possible overall. The detected sensor signals are supplied to the control unit 10 and the control logic 100 in order to calculate therefrom a status of the apparatus 20 with all the relevant components 200. The status denotes on which components 200 and/or at which position or on which component of the apparatus 20 a user intervention has been detected. If, for example, a disposable article is moved into the proximity of the apparatus 20, this is automatically detected using suitable sensors (optical sensors and/or proximity sensors). Passively operated transponders (i.e. without a dedicated power supply) are preferably used as the sensors and transmit the sensor signals detected thereby and the data wirelessly (e.g. via radio waves) to an actively operated receiver (reader), such as for example RFID tags and/or NFC sensors. In dependence upon the calculated status or upon the detected sensor signals, a current and specific graphical and/or textual output is produced in each case in step b for illustration on the display D. The output is output on the display D in step c and can include, for example, at least one newly produced image page 500 having a two-dimensional or three-dimensional illustration of the detected disposable article and additional graphical outputs for the disposable article, e.g. with indications of what to consider when inserting the article into the respective component 200 or into the apparatus 20. Furthermore, markers can occasionally be displayed on the display in order to assist the user during operation. The markers indicate positions on the apparatus 20 and/or positions on the components 200, to which the next operating step is to be applied. Therefore, the status-dependent actuation of the display D also includes a time aspect. The user is thus guided, on the one hand, in terms of the components to be operated and, on the other hand, when these components 200 have to be operated and/or in which sequence. After a display output has been produced and has been displayed on the display D, the further operation of the apparatus 20 can then be monitored via the sensor unit S. This is represented in FIG. 4 by the arrow from step c to step a. Otherwise, the method ends or is run through again. It is important that an amended image page is always output as a status-dependent display output when a status change has been detected on a component 200.

Figure 5:
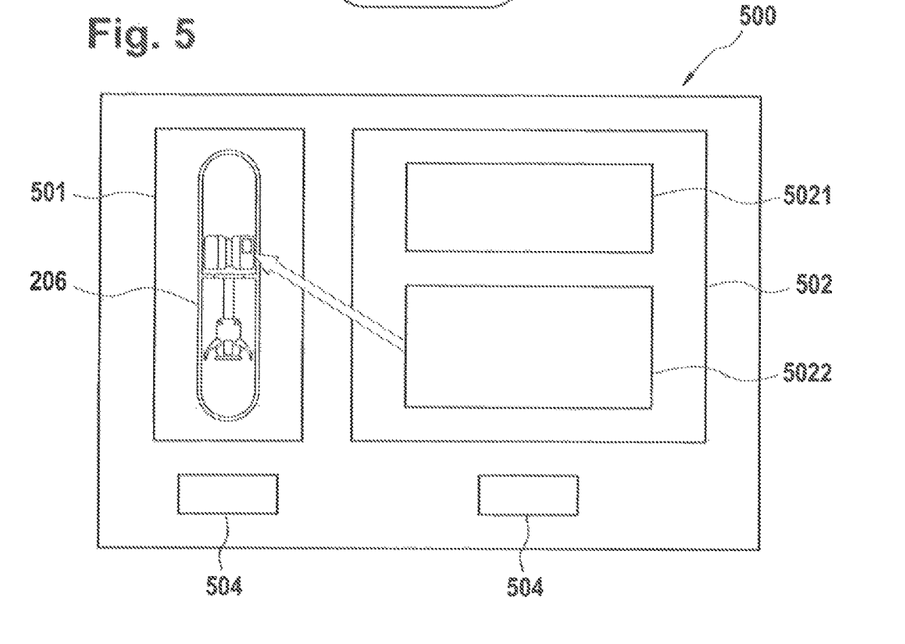
FIG. 5 shows a schematic illustration, by way of example, for a modified screen structure having a status-specific display output.

FIG. 5 shows, by way of example, such a screen output in an application for a heparin pump 206. After the sensor unit S has recognized an intervention on the heparin pump 206 and has detected that a heparin syringe 207 has not yet been inserted, a status-specific output 500 is automatically produced which guides the user in the next steps. The user subsequently inserts a syringe in the syringe holder. This is recognized in accordance with the invention via sensors in the wing holders. Irrespective of the content being displayed on the display D, the display output is now modified in accordance with the invention. In particular, a new image page 500 is output in which a zoomed three-dimensional illustration 501 of the syringe holder (on the left-hand side in FIG. 5) and a status-specific indication field 502 (on the right-hand side in FIG. 5) are displayed. The size, position and/or type of fields can be configured in accordance with the invention. The three-dimensional illustration 501 refers to a technical component (in this case: heparin syringe 207) which is configured for use with a component 200 (in this case: heparin pump 206). The indication field 502 can comprise at least one text field 5021 and/or at least one marker field 5022. The marker field is used to output indications (e.g. In the form of arrows which refer to operating elements which are illustrated on the image illustration 501) to the corresponding positions in the image illustration 501, to which the next operating step is to be applied. Preferably, the content of the text field 5021 corresponds to the indication illustrated in the marker field 5022. The indication can also be in the form of highlighting or marking in the image illustration 501. The image page 500 can additionally also include confirmation fields 504 which are used to detect a confirmation signal input by the user. This confirmation signal can be fed with the signals from the sensor unit S to the control unit 10 for further display actuation. The indication field 502 thus includes all the relevant indications of what to consider when inserting the syringe. The indication field 502 may also includes error indications which advise the user of possible errors in the imminent operation. The indication field can also include, for example, a warning when the sensor unit S has detected that a heparin syringe 207 is to be used without a Luer lock connection. The indication can describe that the connection between the heparin syringe 207 and tube system can be detached and thus represents a potential source of danger.

In order to insert and connect the heparin syringe 207, some operating steps should be performed in a particular sequence on the heparin pump 206. In accordance with the invention, the user is assisted and guided by the outputting of corresponding indications 502 on the display D in the corresponding sequence. For example, the following indications can be output in field 502 with a corresponding marking, allocated to each component, in field 501:

connect heparin syringe 207 to the arterial tube system;
move handle 2064 to the lower position by pressing the clamping levers 2065;
insert heparin syringe 207 between the tension levers 2061. The wings 2071 of the syringe cylinder must be located between the tension levers 2061 and the bracket 2062;

move handle 2064 to the starting position by pressing the clamping levers 2065. The plunger 2072 of the syringe piston must be located between the clamps 2063 of the handle 2064;

if the plunger of the syringe piston can no longer be displaced by pressing the clamping levers, the heparin syringe 207 is correctly fixed.

if it is still closed, open the clamp of the heparin line.

For the latter application, provision is made in an advantageous embodiment of the invention that the opening of the clamp for the heparin line or the status of the clamp as the component 200 is detected via a corresponding sensor in order to automatically display the allocated menu or the respective image page 500 on the display D.

If, for example, the cover 204 of the extracorporeal blood treatment module is opened during the treatment, this is automatically detected by sensors of the sensor unit S which are arranged, for example, on the doors or covers 204, and is relayed to the control unit 10. This indicates an unscheduled intervention. In accordance with the invention, operating options corresponding to the probable situation can be displayed to the user on the display D, such as for example to interrupt the treatment and indications to place the apparatus 20 in a secure state. The blood pump is thereby stopped and the patient is separated from the extracorporeal blood circulation module at the venous and arterial access points by tube clamps to be activated. It has proved to be advantageous that the apparatus 20 can be operated, even in emergencies, very quickly, purposefully, and simply, even by a less experienced person since a step-wise instruction of the operating steps can be output, specific to the situation. This embodiment increases patient safety.

According to a preferred embodiment of the invention, the operating elements and switches of the apparatus 20, which are to be operated in an emergency, are illustrated in a highlighted manner in prominent positions on the display D (e.g. by an enlarged or flashing illustration, a different color system or by a corresponding animation).

According to a preferred embodiment of the invention, the produced display output 500 remains superimposed until the user confirms or acknowledges, on one of the confirmation fields 504, a final query at the end of a description that another operation is planned and e.g. a heparin syringe is not to be used. Then, a new image page 500 can be produced which prompts the user to remove the partially inserted or mistakenly inserted syringe. This intervention is also detected by the sensor unit S.

In an advantageous embodiment, the method can be interrupted so as to perform a check and/or correction. Provision is thus made that the user (once again) removes the syringe 207 from the heparin pump 206 for example so as to perform a correction and is then inserted again. This is recognized by a sensor. Preferably, the time reference is also detected, so that the sensor unit S also detects when and how often a component 200, in this case the heparin pump 206, has been operated. These signals can be calculated in the control unit 10 such that the produced image page 500 is further illustrated with indications to insert the heparin syringe 207. For example, after inserting the syringe, a so-called initial heparin coupling test is performed, in which approximately 0.5 ml of heparin solution is administered. Prior to performing the coupling test, the user should monitor the administered heparin volume in the syringe because, in this case, the conveyed volume can deviate from the above-mentioned amount. This monitoring step can be output on the produced image page 500. Optionally, a statement can be output that the conveyed volume has to be considered, if need be, when calculating the overall amount of heparin. During treatment, the heparin coupling test is automatically repeated when inserting or changing the syringe and when changing the arterial tube system, with the allocated image pages 500 on the display D.

In another advantageous embodiment of the invention, the produced display, output and the allocated status are stored in a memory. This has the advantage that the output can also be retrieved directly from the memory for other instances, if the respective status occurs again. If, in the above example, an error occurs at a subsequent point in time—after removing and re-inserting the syringe 207 into the heparin pump 206—said error requiring the syringe to be inserted again, then for the purpose of error analysis prior to or during the re-inserting of the syringe the respective image page 500 can remain displayed or can be displayed again if other image pages have been output in the meantime.

In an advantageous embodiment, a produced image page 500 can also be stored so as to be able to illustrate other menus on the display D. Furthermore, the image page 500 and/or the illustrations and/or fields 501, 502, 5021, 5022, 504 produced therefor and made available for, and output to, the user as preparatory indications.

In another advantageous embodiment of the invention, a correction button is provided on the produced image page 500. When actuating the correction button, the produced image page 500 remains illustrated or the image page produced in the immediately preceding step is returned in order to assist the user in the immediately preceding step if this step must be carried out again in the corrected fashion.

In another advantageous embodiment of the invention, the control unit 10 additionally comprises an authorization module which is configured to exchange data with a proximity sensor and detect the authorization of an operating person approaching the apparatus 20. To this end, identification units can be provided which are worn by the operating personnel and are used to uniquely identify the person and to determine the authorization thereof in relation to the operation of the apparatus. The identification units can be integrated in other electronic components (mobile telephone smart-card, smart-watch, watch, etc.). The data from the identification units can be transmitted, for example, via suitable wireless communication channels, e.g. radio wave-based channels such as NFC or RFID, or via Bluetooth or other protocols for wirelessly exchanging data. The control unit 10 is configured to then, in accordance with the invention, produce a situation-dependent and status-based output on the display D. The authorization of the operating person also influences the status, so that only those operating steps for which the approaching operating person is also authorized to carry out are displayed.

In an exemplary embodiment, the use of pump rotors as components 200 is to he monitored. Tube roller pumps of the dialysis apparatuses 20 are fitted with spring-mounted rollers which can move in the radial direction. The former causes, in the event that the fluid path is blocked downstream of the tube roller pump, an inadmissibly high pressure in the liquid (blood) to be pumped which can lead on the one hand to the blood being damaged by hemolysis and on the other hand to potential tube ruptures as a result of excess pressure. Owing to the spring-mounting of the roller, the complete occlusion of the tube is compensated for by the roller when the liquid pressure exceeds the contact pressure of the roller and thus limits the maximum liquid pressure to the contact pressure determined by the spring-mounted system. This can differ depending upon the treatment. For example, for pediatric treatments specific pump rotors are used. For this purpose, the pump rotors are interchangeable and in accordance with the invention can have identification devices which can be provided, for example, as a component of the sensor unit S. The identification device is used such that the control unit 10 can automatically detect which rotor is used (for example, as described in German Patent Application No. DE 20 2010 002 133 A1, the entire disclosure of which is hereby incorporated by reference herein). The radially movable rotor arms of the pump can be pressed together when setting up the machine or the apparatus 20 in order to facilitate the insertion of the tube in the pump bed.

In accordance with the invention, in a first retrospective variant of the invention, all or selected, already performed operations on the medical apparatus 20 and on the components 200 thereof are detected by the sensor unit S and are used for the status-dependent display output-in the above example, i.e., for the operation of the apparatus 20 for changing the rotor and also for the operation by pressing together the rotor arms, as described above. For this, suitable sensors of the sensor unit S are provided in accordance with the invention. These are used to detect the process on the apparatus 20 or the operating steps performed on the apparatus and the components 200 thereof The performed operating steps are represented in a status. On the basis thereof and in accordance with the invention, a status-based output is produced on the display D.

In accordance with the invention, in a second prospective variant of the invention, the detected and already performed operations on the medical apparatus 20 and on the components 200 thereof are used by the sensor unit S in order to calculate therefrom future probable further operating steps and to use same for the status-dependent display output. File status then includes not only the already performed operating steps but also future or probably intended operating steps. To this end, a memory can be provided which for calculation purposes is accessed by a statistical algorithm and in which reference data are stored. For instance, a consequence status can always be stored as a reference in relation to a detected status and can be accessed by the algorithm. If, for example, specific sensor signals are detected by the sensor unit 5, which signals define a status which can be inferred from the implementation of paediatric treatment, then in accordance with the invention a display output having a specific paediatric menu is automatically produced. In contrast, if "planned insertion of tube" is detected as the status, then in accordance with the invention a step-by step instruction for inserting the tube for the respective pump is output. A differentiation between the respective components 200 can also preferably be made (i.e. for example differentiated for a blood pump in single-needle operation or in double-needle operation or for a substitute fluid pump).

In an embodiment of the invention, the illustration on the display D is thus triggered by the sensor data from the sensor unit S. Therefore, the technical advantage is achieved that output signals are produced which are specifically matched to the detected status of the apparatus 20 with the components 200 thereof. It is no longer required to run through a preconfigured menu which allows a considerable time saving to be made.

in another exemplary embodiment, the method in accordance with the invention is applied to a holding device for a dialysis filter as a component 200. For this purpose, sensors are provided which recognize whether a dialyzer is inserted. Depending upon whether a dialyzer is detected as being inserted and optionally whether a dialyzer type is detected, a specific display is displayed for the further operating steps. The dialyzer type can be determined, e.g., by polling sensor data which measure an opening angle of a clamp of the apparatus 20.

Exemplary embodiments of the invention determine an apparatus state on the basis of automatically detected sensor signals which includes all component states (or only those ones which are configured to be relevant) (e.g. valve 1 open, valve 2 closed, switch 1 on, switch 2 off, cover open, etc.). An output is produced for the display on the basis of the determined status. This can be an image page 500 which is used as a start page for a particular operating menu.

It is noted that the description of the invention and the exemplary embodiments are fundamentally to be understood to be non-limiting with respect to a specific physical implementation of the invention. All features explained and illustrated with reference to individual embodiments of the invention can be provided in different combinations in the subject matter in accordance with the invention in order to achieve the advantageous effects thereof at the same time. Therefore, it is e.g. also within the scope for the invention to check the correct operation not only of the heparin pump but also of other components 200 of the medical apparatus 20. These can include, e.g., manually operated components or automatic elements. For a person skilled in the art, it will be appreciated that the invention can be used not just for dialysis apparatuses but also for other medical apparatuses which are operated and controlled via a display D.

Furthermore, the components of the medical apparatus 20 can be implemented in a plurality of physical products for the status-dependent control of the medical apparatus 20 via an adaptively produced display output.

The scope of protection of the present invention is set by the claims and is not limited by the features explained in the description or shown in the figures.

It will be appreciated by those of skill in the art that the execution of the various machine-implemented processes and steps described herein may occur via the computerized execution of processor-executable instructions stored on a non-transitory computer-readable medium, e.g., random access memory (RAM), read-only memory (ROM), programmable read-only memory (PROM), volatile, nonvolatile, or other electronic memory mechanism. Thus, for example, the operations described herein performed by computing devices and components thereof may be carried out according to stored instructions and/or installed applications.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A medical apparatus, comprising:
a plurality of components;
one or more sensors corresponding to one or more of the plurality of components, configured to detect signals;
a display; and
a controller, configured to:
receive signals from the one or more sensors,
determine, from the signals, a current status of the medical apparatus,
determine, based on the current status of the medical apparatus, a predicted status of the medical apparatus, and
determine control commands for the display based on the determined predicted status for status-dependent control of the display;
wherein the display is configured to display the determined control commands;
wherein the current status of the medical apparatus comprises the medical apparatus being open; and
wherein determining the predicted status of the medical apparatus comprises determining that the medical apparatus will undergo maintenance based on the medical apparatus being open and further based on maintenance planning data.

2. The medical apparatus according to claim 1, wherein the plurality of components comprises a heparin pump configured for receiving a heparin syringe, a holding device for a dialysis filter and/or a receiving device for disposable medical articles.

3. The medical apparatus according to claim 1, wherein the one or more sensors comprise a plurality of sensors disposed on different components and/or at different positions of the medical apparatus.

4. The medical apparatus according to claim 1, wherein the one or more sensors comprise a plurality of sensors configured to detect different physical or chemical measurement variables.

5. The medical apparatus according to claim 1, wherein the one or more sensors comprise at least one sensor, switch, button and/or potentiometer.

6. The medical apparatus according to claim 1, wherein the controller comprises a sensor trigger switch configured for activating and deactivating the one or more sensors.

7. The medical apparatus according to claim 1, wherein determining control commands for the display comprises determining a specific user interface menu for the display corresponding to a component of the medical apparatus predicted to undergo maintenance based on the maintenance planning data.

8. A method for controlling a display of a medical apparatus, comprising:
detecting, via one or more sensors of the medical apparatus, sensor data which represent a current status of the medical apparatus;
determining, by a controller of the medical apparatus, based on the current status of the medical apparatus, a predicted status of the medical apparatus;
determining, by the controller of the medical apparatus, control commands for controlling the display based on the predicted status of the medical apparatus; and
displaying, by the display of the medical apparatus, the determined control commands;
wherein the current status of the medical apparatus comprises the medical apparatus being open; and
wherein determining the predicted status of the medical apparatus comprises determining that the medical apparatus will undergo maintenance based on the medical apparatus being open and further based on maintenance planning data.

9. The method according to claim 8, wherein the current status of the medical apparatus includes at least one status variable and wherein each status variable denotes a current status of a component of the medical apparatus.

10. The method according to claim 8, wherein operation of a component of the medical apparatus comprises a sequence of operating steps, and each operating step is allocated to at least one display output.

11. The method according to claim 8, wherein an output on the display comprises an interactive user guide with a sequence of operating menu illustrations with sub-menu illustrations, wherein the sequence of operating menu illustrations is determined based on the detected sensor data.

12. The method according to claim 8, wherein an output on the display is configured for interactively guiding a user during operation or during setup of the medical apparatus, and wherein an operating menu illustration is selected to be displayed for a component of the medical apparatus based on the detected sensor data corresponding to detection of a status change.

13. A non-transitory computer-readable medium having processor-executable instructions stored thereon for controlling a display of a medical apparatus, the processor-executable instructions, when executed, facilitating performance of the following:
detecting, via one or more sensors of the medical apparatus, sensor data which represent a current status of the medical apparatus;
determining, by a controller of the medical apparatus, based on the current status of the medical apparatus, a predicted status of the medical apparatus;
determining, by the controller of the medical apparatus, control commands for controlling the display based on the predicted status of the medical apparatus; and
displaying, by the display of the medical apparatus, the determined control commands;
wherein the current status of the medical apparatus comprises the medical apparatus being open; and
wherein determining the predicted status of the medical apparatus comprises determining that the medical apparatus will undergo maintenance based on the medical apparatus being open and further based on maintenance planning data.

14. The non-transitory computer-readable medium according to claim 13, wherein the current status of the medical apparatus includes at least one status variable and wherein each status variable denotes a current status of a component of the medical apparatus.

15. The non-transitory computer-readable medium according to claim 13, wherein operation of a component of the medical apparatus comprises a sequence of operating steps, and each operating step is allocated to at least one display output.

16. The non-transitory computer-readable medium according to claim 13, wherein an output on the display comprises an interactive user guide with a sequence of operating menu illustrations with sub-menu illustrations, wherein the sequence of operating menu illustrations is determined based on the detected sensor data.

17. The non-transitory computer-readable medium according to claim 13, wherein an output on the display is configured for interactively guiding a user during operation or during setup of the medical apparatus, and wherein an operating menu illustration is selected to be displayed for a component of the medical apparatus based on the detected sensor data corresponding to detection of a status change.

* * * * *